United States Patent [19]

Kuroda et al.

[11] Patent Number: 4,877,703
[45] Date of Patent: Oct. 31, 1989

[54] PHOTOCONDUCTOR FOR ELECTROPHOTOGRAPHY HAVING A SQUARYLIUM CHARGE GENERATING DYE

[75] Inventors: Masami Kuroda; Yoshimasa Hattori; Noboru Furusho; Yoshinobu Sugata, all of Kawasaki, Japan

[73] Assignee: Fuji Electric Co., Ltd., Kawasaki, Japan

[21] Appl. No.: 284,335

[22] Filed: Dec. 14, 1988

[30] Foreign Application Priority Data

Dec. 16, 1987 [JP] Japan .................. 62-317768
Apr. 26, 1988 [JP] Japan .................. 62-103678

[51] Int. Cl.$^4$ ............................................ G03G 15/06
[52] U.S. Cl. .................................... 430/76; 430/58
[58] Field of Search .................. 430/58, 73, 74, 76

[56] References Cited

U.S. PATENT DOCUMENTS

| | | | |
|---|---|---|---|
| 3,484,237 | 12/1969 | Shattuck et al. | 430/76 |
| 4,278,747 | 7/1981 | Murayama et al. | 430/82 |
| 4,367,273 | 1/1983 | Murayama et al. | 430/82 |
| 4,606,986 | 8/1986 | Yanus et al. | 430/59 |
| 4,624,904 | 11/1986 | Kazmaier et al. | 430/59 |
| 4,677,045 | 6/1987 | Champ et al. | 430/76 |

FOREIGN PATENT DOCUMENTS 3754372 3/1972 Japan .
1078572 7/1972 Japan .

*Primary Examiner*—John L. Goodrow
*Attorney, Agent, or Firm*—Spencer & Frank

[57] ABSTRACT

A photoconductor for electrophotography comprising a novel squarylium as a charge generating substance. A squarylium compound is represented by the following general formula:

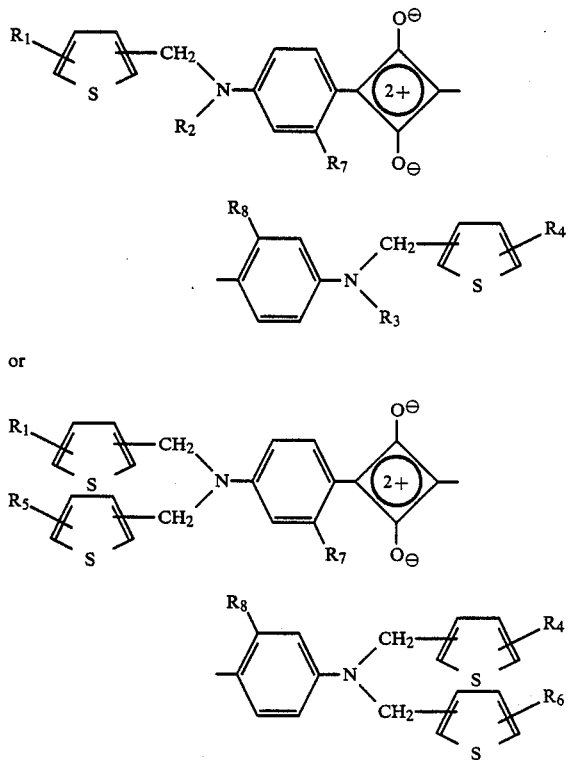

wherein, each of $R_1$, $R_2$, $R_3$, $R_4$, $R_5$ and $R_6$ stands for a hydrogen atom, a halogen atom, an alkyl group, an aryl group, or a nitro group, and each of $R_7$ and $R_8$ stands for a hydrogen atom or a hydroxy group.

9 Claims, 1 Drawing Sheet

PHOTOCONDUCTOR FOR ELECTROPHOTOGRAPHY HAVING A SQUARYLIUM CHARGE GENERATING DYE

BACKGROUND OF THE INVENTION

1. Field of the Invention

The present invention relates to photoconductors for electrophotography, and particularly to a photoconductor for electrophotography which contains a squarylium compound in the photosensitie layer thereof formed on an electroconductive substrate.

2. Description of the Prior Art

Photosensitie materials which have heretofore been used in photoconductors for electrophotography include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazole and polyvinylanthracene, organic photoconductive substances such as phthalocyanine compounds and disazo compounds, and dispersions of such organic polymeric photoconductive substances in resin binder and films of organic photoconductive substance as mentioned above, deposited by means of vacuum evaporation.

Photoconductors are required to have a function of maintaining a surface electric charge in the dark, a function of generating an electric charge upon receiving light, and a function of transporting an electric charge upon receiving light. They are classified into two types of photoconductors, namely so-called monolayer type photoconductors, and so-called laminate type photoconductors. The former comprises a single layer having all of the above-mentioned three functions, and the latter comprises functionally distinguishable laminated layers, one of which contributes mainly to the generation of electric charge, and another of which contributes to the retention of surface electric charge in the dark and the electric charge transportation upon receiving light. In an electrophotographic method using a photoconductor of the kind as mentioned above, for example, the Carlson's system is applied to image formation. The image formation according to this system comprises steps of subjecting a photoconductor in the dark to corona discharge to charge the photoconductor, exposing the surface of the charged photoconductor with imagewise light based on a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photoconductor is subjected to the steps of removal of the electric charge, removal of the remaining toner (cleaning), neutralizaiton of the residual charge with light (erasion), and so on to be ready for reuse.

Photoconductors for electrophotography in which use is made of an organic materials(s) have recently been put into practical use by virtue of the advantageous feature(s) of flexibility, thermal stability, and/or a film forming capacity. They include a photoconductor comprising poly-N-vinylcarbazole and 2,4,7-trinitrofluoren-9-one (disclosed in U.S. Pat. No. 3,484,237), a photoconductor using an organic pigment as a main component (disclosed in Japanese patent laid-open No. 37,543/1972), and a photoconductor using as a main component a eutectic complex composed of a dye and a resin (disclosed in Japanese patent laid-open No. 10,785/1975). A number of novel hydrazone compounds and disazo compounds and the like have also been put into practical use for photoconductors.

Although organic materials have many advantageous features mentioned above wtih which inorganic materials are not endowed, however, the fact is that there have been obtained no organic materials fully satisfying all the characteristics required of a material to be used in photoconductors for electrophotography at the present. Particular problems involved in organic materials have been concerned with photosensitivity and characteristics in continuous repeated use.

SUMMARY OF THE INVENTION

An object of the present invention is to provide a photoconductor for electrophotography for use in copying apparatus and printers which photoconductor includes a novel organic materials not used to date as a charge generating substance in the photosensitive layer, and has a high photosensitivity and excellent characteristics in repeated use.

In the first aspect of the present invention, a photoconductor for electrophotography comprises:

at least one squarylium compound represented by the following general formula (I) as a charge generating substance:

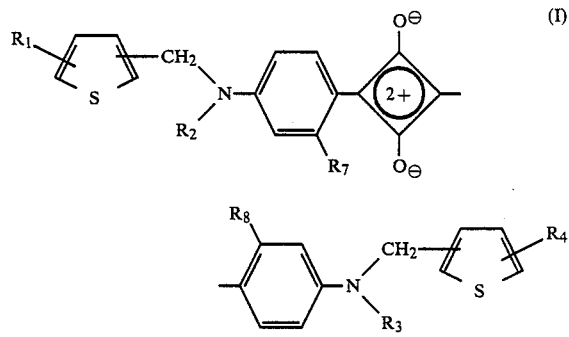

wherein, each of $R_1$, $R_2$, $R_3$ and $R_4$ stands for a hydrogen atom, a haloen atom, an alkyl grup, an aryl group, or a nitro group, and each of $R_7$ and $R_8$ stand for a hydrogen atom or a hydroxy group.

Here, the photoconductor may comprise a layer including dispersion of a charge generating substance selected from suarylium compounds represented by the general formula (I) and a charge transporting substance.

The photoconductor may comprise a laminate of a charge transporting layer mainly composed of a charge transporting substance and a charge generating layer including a compound selected from squarylium compounds represented by the general formula (I).

In the second aspect of the present invention, a photoconductor for electrophotography comprises:

at least one squarylium compound represented by the following general formula (II) as a charge generating substance:

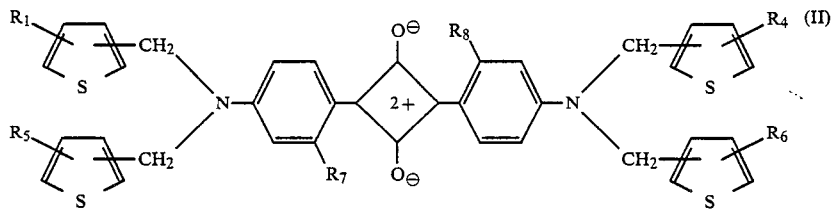

wherein, each of $R_1$, $R_2$, $R_3$, $R_4$, $R_5$ and $R_6$ stands for a hydrogen atom, a halogen atom, an alkyl grup, an aryl group, or a nitro group, and $R_7$ and $R_8$ stand for a hydrogen atom and a hydroxy group, respectively.

Here, the photoconductor may comprise a layer including dispersion of a charge generating substance selected from squarylium compounds represented by the general formula (II) and a charge transporting substance.

The photoconductor may comprise a laminate of a charge transportin layer mainly composed of a charge transporting substance and a charge generating layer including a compound selected from squarylium compounds represented by the general formula (II).

In the third aspect of the present invention, a photoconductor for electrophotography commprises:

at least one squarylium compound represented by the following general formula (III) as a charge generating substrate:

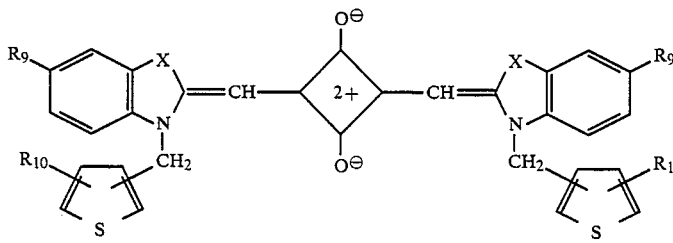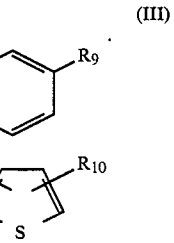

wherein, each of $R_9$ and $R_{10}$ stands for a hydrogen atom, a halogen atom, a nitro group, an alkoxy group, an unsubstituted or substituted aryl group, or an unsubstituted or substituted alkyl group; X stands for an oxygen atom, a sulfur atom, a selenium atom, or a dimethylmethylene group.

Here, the photoconductor may comprise a layer including a dispersion of a charge generating substance selected from squarylium compounds represented by the general formulae (III) and a charge transporting substance.

The photoconductor may comprise a laminate of a charge transporting layer mainly composed of a charge transporting substance and a charge generating layer including a compound selected from squarylium compounds represented by the general formulae (III).

The above and other objects, effects, features and advantages of the present invention will become more apparent from the following description of embodiments thereof taken in conjunction with the accompanying drawings.

DETAILED DESCRIPTION OF PREFERRED EMBODIMENTS

Figure 1:
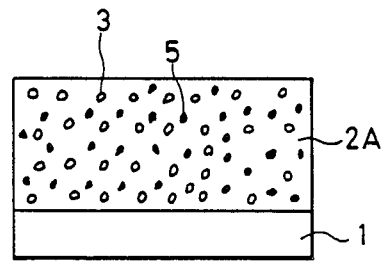
FIGS. 1 to 3 are schematic cross-sectional views of photoconductors according to the present invention.
Figure 2:
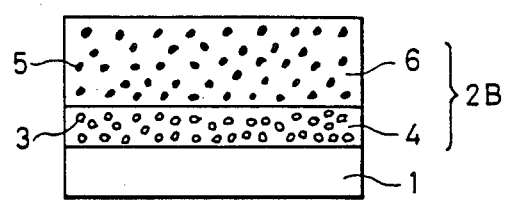
Figure 3:
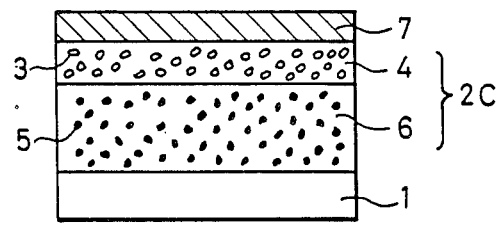

The photoconductor of the present invention, which contains a squarylium compound in the photosensitive layer thereof, may have ane one of the structures as shown in FIGS. 1, 2 and 3 according to the manner of application thereto the squarylium compound.

FIGS. 1, 2 and 3 are schematic cross-sectional views of different embodiments of the photoconductor of the present invention, respectively.

FIG. 1 shows a cross-sectional view of a monolayer type photoconductor. A photosensitive layer 22A is provided on an electronconductive substrate 1. The photosensitive layer 2A comprises a squarylium compound as a charge generating substance 3 and a charge transporting substance 5 both of which substances are dispersed in a resin binder matrix so that the photosensitive layer 2A functions as photoconductor.

FIG. 2 shows a cross-sectional view of a laminate type photoconductor. A laminated photosensitive layer, 2B is provided on an electroconductive substrate 1, a lower layer of the laminate is a charge generating layer 4 including a squarylium compound 3 as a charge generating substance and an upper one is a charge transporting layer 6 containing a charge transporting substance 5 as a main component, so that the photosensitive layer 2B functions as a photoconductor. This photoconductor is usually used according to the negative charge mode.

FIG. 3 shows a cross-sectional view of another laminate type photoconductor having a layer structure in reverse to that of FIG. 2. A laminated photosensitive layer 2C is provided on an electroconductive substrate 1, a lower layer of the laminate is a charge transporting layer 6 and an upper one is a charge generating layer 4 including a squarylium compound as a charge generating substance 3. The photosensitive layer also functions as a photoconductor. This photoconductor is usually used according to the positive charge mode. In this case, a covering layer 7 may generally be further provided as shown in FIG. 3 to protect the charge generating layer 4.

Thus, two kinds of layer structure are provided for laminate type photoconductors. The reason for this is that, even if any photoconductor with the layer structure as shown in FIG. 2 is to be used in the positive charge mode, no charge transporting substances adaptable to the positive charge mode have been found yet. Accordingly, when any laminate type photoconductor is to be used in the positive charge mode, the photoconductor is required of a layer structure as shown in FIG. 3 for the present.

A photoconductor as shown in FIG. 1 can be produced by dispersing a charge generating substance in a solution of a charge transporting substance and a resin binder and applying the resulting dispersion on an electroconductive substrate and then drying the resulting coating film.

A photoconductor as shown in FIG. 2 can be prepared by applying and drying a dispersion of a particulate charge of generating substance in a solvent and/or a resin binder on an electroconductive substrate, followed by applying a solution of a charge transporting substance and a resin binder on the resulting layer and drying.

A photoconductor as shown in FIG. 3 can be prepared by applying and drying a solution of a charge transporting substance and a resin binder onto an electroconductive substrate, and coating and drying a dispersion of a particulate charge generating substance in a solvent and/or a resin binder onto the resulting coating layer, followed by formation of a covering layer.

The electroconductive substrate 1 serves as an electrode of the photoconductive and as a support for a layer(s) formed thereon. The electroconductive substrate may be in the form of a cylinder, a plate or a film, and may be made of a metallic material such as aluminum, stainless steel or nickel, or other material having a surface treated to be electroconductive, such as glass so treated or a resin so treated.

The charge generating layer 4 is formed by application of a dispersion of a squarylium compound as a charge generating substance 3 in a resin binder, and this layer generates an electric charge upon receiving light. It is important that the charge generating layer 4 be high not only in charge generating efficiency but also in capability of injecting the generated electric charge into the charge transporting layer 6 and any covering layer 7, which capability is desirably as little dependent upon the electric field as possible and high even in low intensity electric fields. It also is possible to form a charge generating layer using a charge generating substance as a main component in mixture with a charge transporting substance and so on. Resin binders usable in the charge generating layer include polycarbonates, polyesters, polyamides, polyurethanes, epoxy resins, silicone resins, and homopolymers and copolymers of methacrylic esters, which may be used either alone or in appropriate combination.

The charge transporting layer 6, which is formed by application of a solution or dispersion of a hydrazone compound, a pyrazoline compound, a styryl compound, a triphenyl-amine compound, an oxazole compound or an oxadiazole compound as an organic charge transporting substance in a resin binder, exhibits a function of serving as an insulating layer in the dark to retain an electric charge of the photoconductor as well as a function transporting an electric charge injected from the charge generating layer upon receiving light. Resin binders usable in the charge transporting layer include polycarbonates, polyesters, polyamides, polyurethanes, epoxy resins, silicone resins, and homopolymers and copolymers of methacrylic ester.

The covering layer 7 has a function of receiving and retaining an electric charge generated by corona discharge in the dark and a capability of transmitting light to which the charge generating layer should respond. It is necessary that the convering layer 7 transmits light upon exposure of the photoconductor and allows the light to reach the charge generating layer, and then undergoes the injection of an electric charge generated in the charge generating layer to nuetralize and erases a surface electric charge. Materials usable in the covering layer include organic insulating film-forming materials such as polyesters and polyamides. Such organic materials may also be used in mixture with an inorganic material such as a glass resin or $SiO_2$, or an electric resistance-lowering material such as a metal or a metallic oxide. Materials usable in the covering layer are not limited to organic insulating film-forming materials, and further include inorganic materials such as $SiO_2$, metals, and metallic oxides, which may be formed into a covering layer by an appropriate method such as vacuum evaporation and deposition, or sputtering. From the viewpoint of the aforementioned description, it is desirable that the material to be used in the covering layer be as transparent as possible in the wavelength range wherein the charge generating substance attains maximum light absorption.

Although the thickness of the covering layer depends on the material or composition thereof, it can be arbitrarily set in so far as it does not produce any adverse effects including an increase in a residual potential in continuous repeated use.

Description will now be made of photoconductors using a squarylium compound. The first group of squarylium compounds to be used in the present invention are represented by one of the following general formulae (I) and (II).

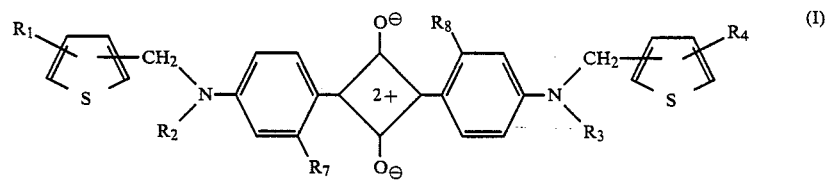
(I)

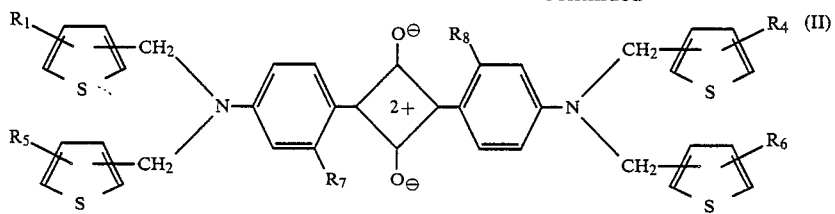

-continued (II)

Wherein, each of $R_1$, $R_2$, $R_3$, $R_4$, $R_5$ and $R_6$ stands for a hydrogen atom, a halogen atom, an alkyl group, an aryl group, or a nitro group, each of $R_7$ and $R_8$ stands for a hydrogen atom or a hydroxy group.

These squarylium compounds represented by the general formulae (I) and (II) can be synthesized according to the following process; that is an amino compound represented by the general formula

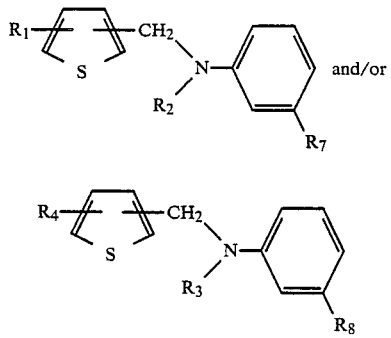

and/or

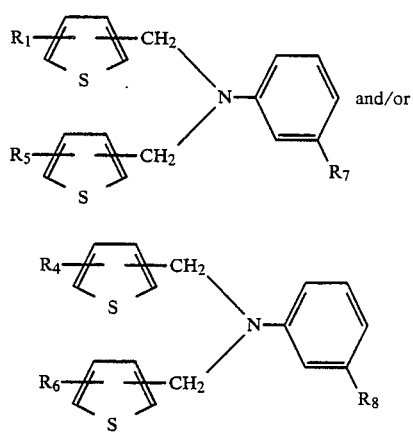

and/or is dehydration reacted with 3,4-dihydroxy-3-cyclobutene-1,2-dione in a suitable organic solvent such as a mixed solvent of 1-butanol and benzene.

Specific examples of squarylium compounds of the general formula (I) or (II) prepared in the above-mentioned manner include:

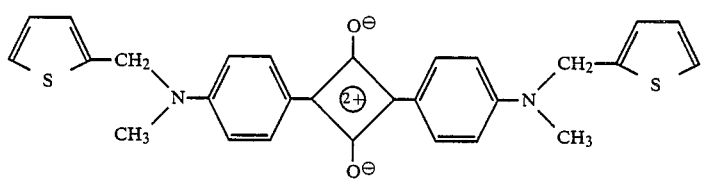

Compound No. I-1

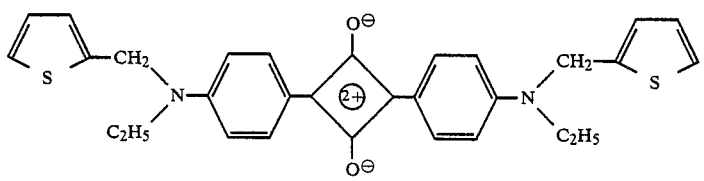

Compound No. I-2

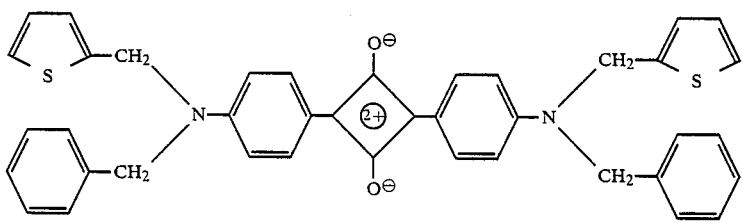

Compound No. I-3

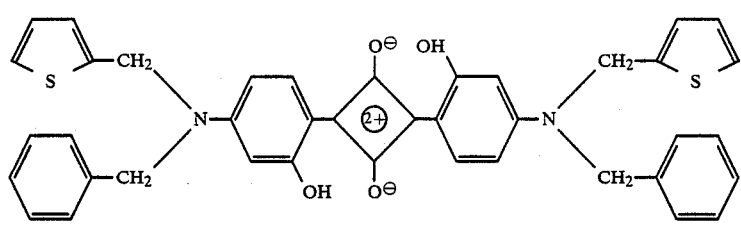
Compound No. I-4
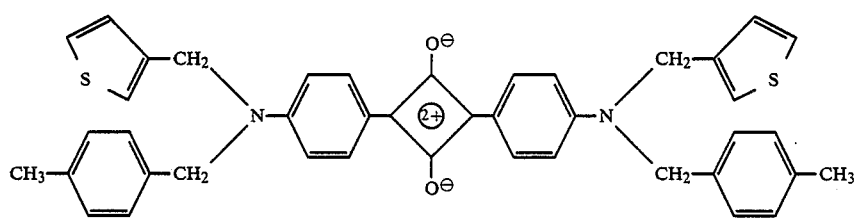
Compound No. I-5
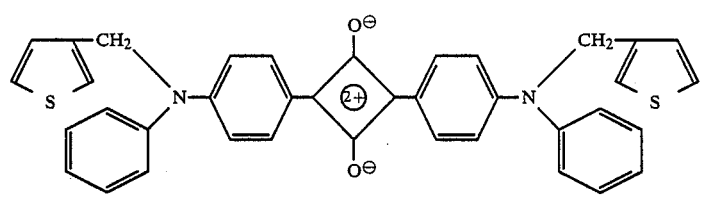
Compound No. I-6
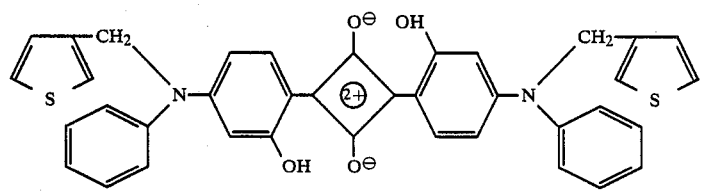
Compound No. I-7
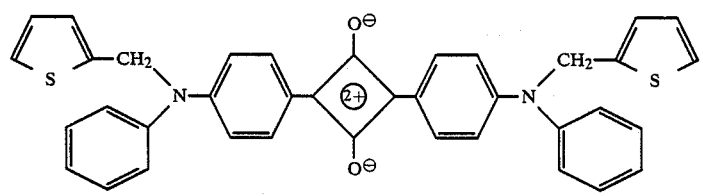
Compound No. I-8
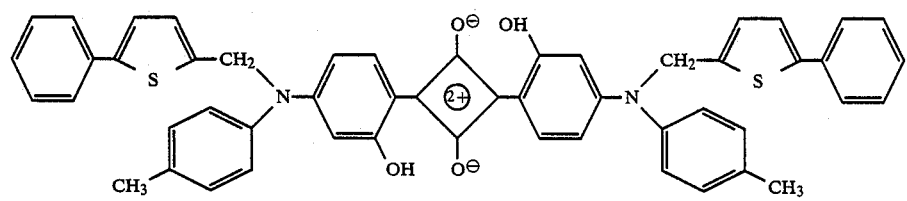
Compound No. I-9
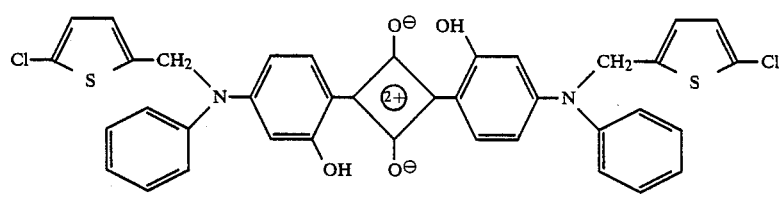
Compound No. I-10

-continued
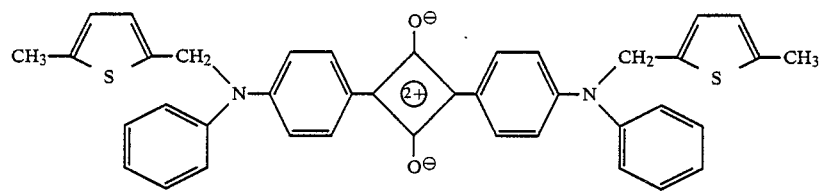
Compound No. I-11
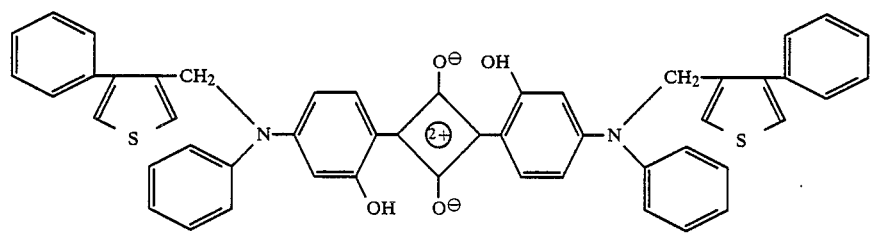
Compound No. I-12
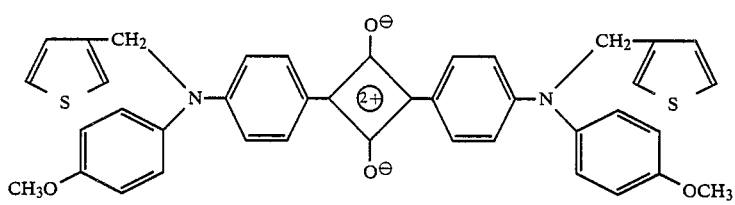
Compound No. I-13
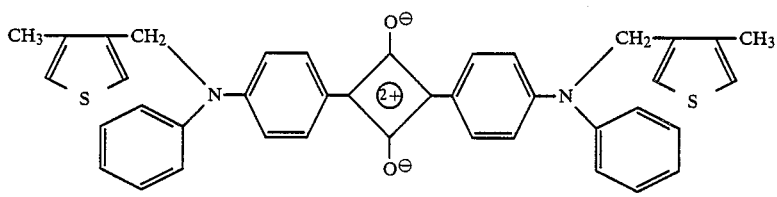
Compound No. I-14
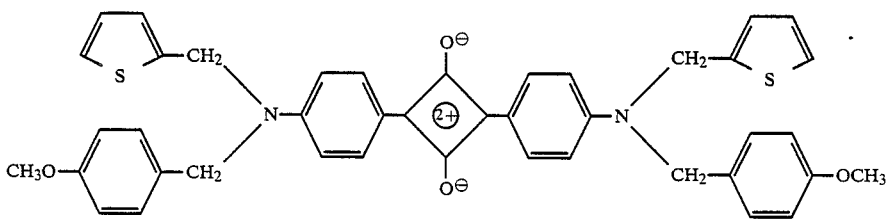
Compound No. I-15
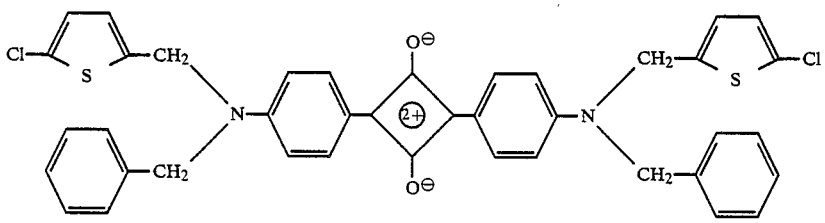
Compound No. I-16
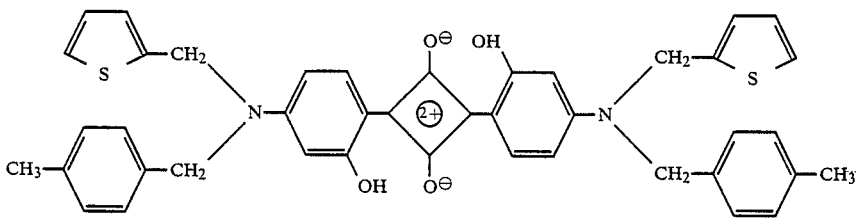
Compound No. I-17

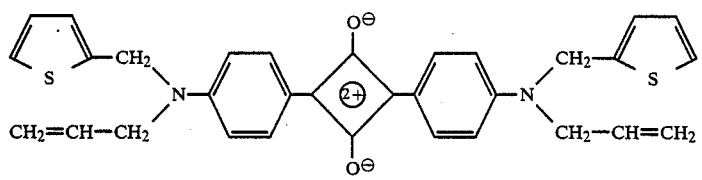
Compound No. I-18
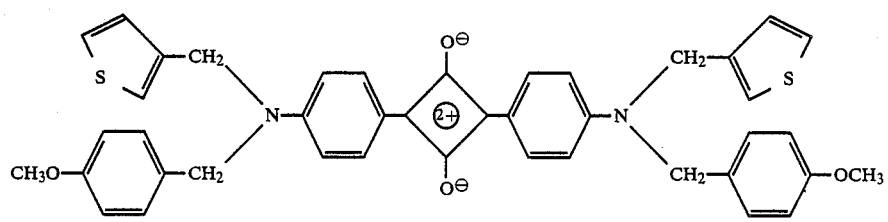
Compound No. I-19
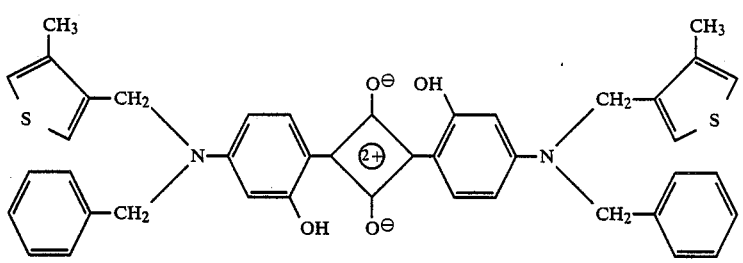
Compound No. I-20
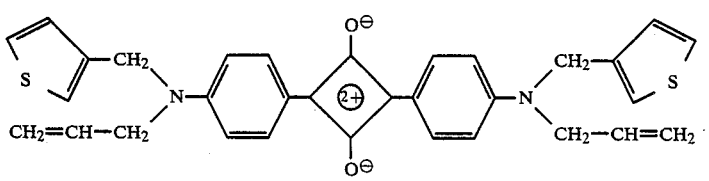
Compound No. I-21
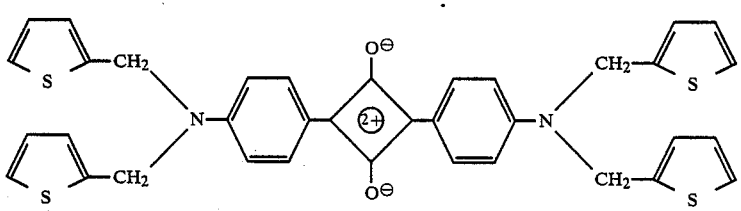
Compound No. I-22
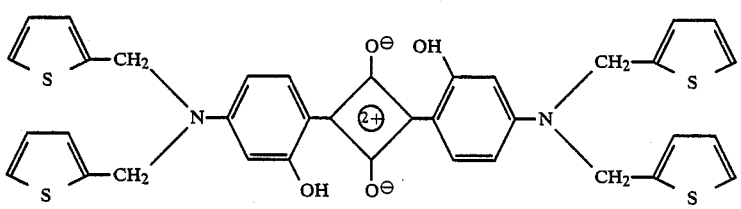
Compound No. I-23
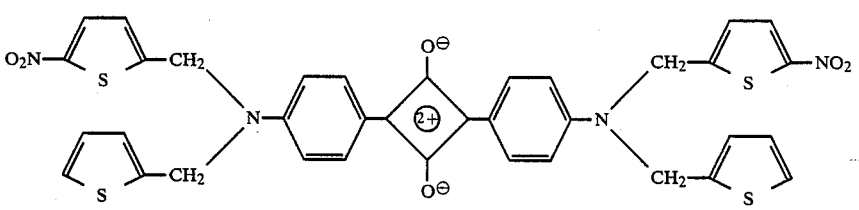
Compound No. I-24

-continued
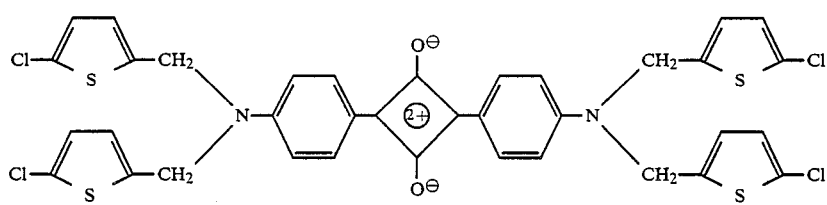
Compound No. I-25
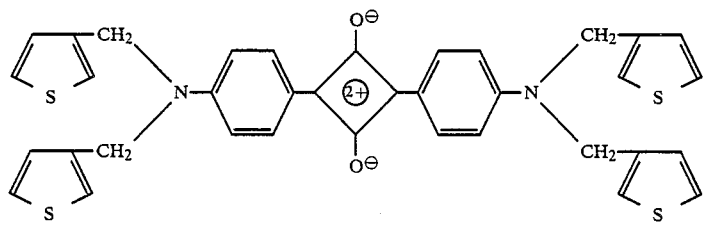
Compound No. I-26
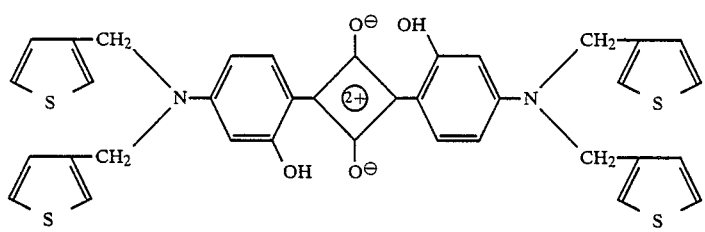
Compound No. I-27
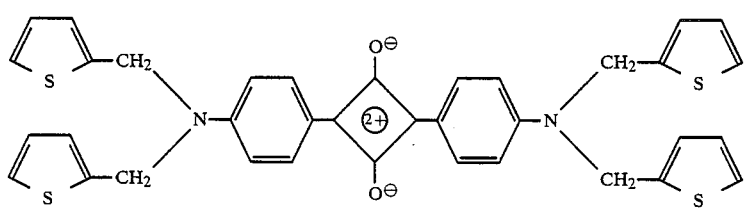
Compound No. I-28
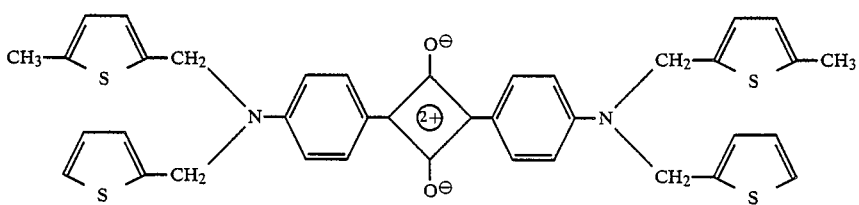
Compound No. I-29
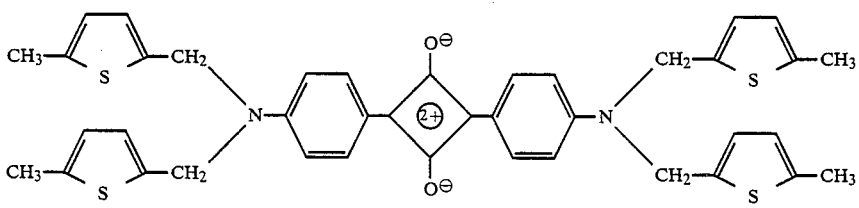
Compound No. I-30
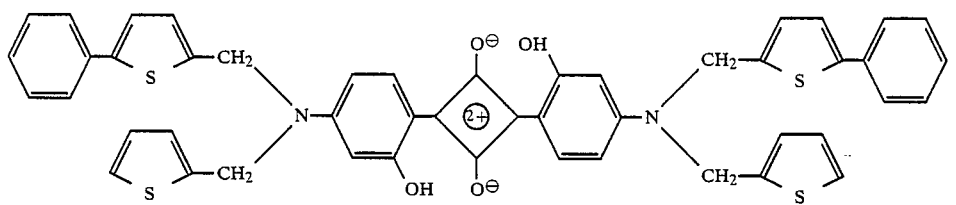
Compound No. I-31

-continued

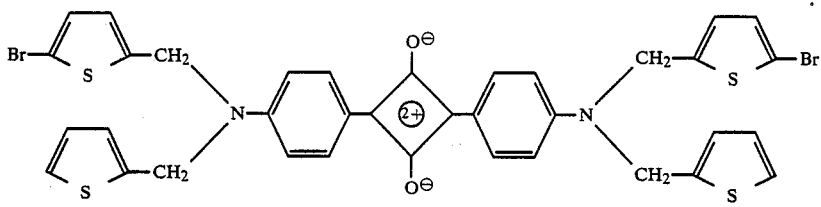

Compound No. I-32

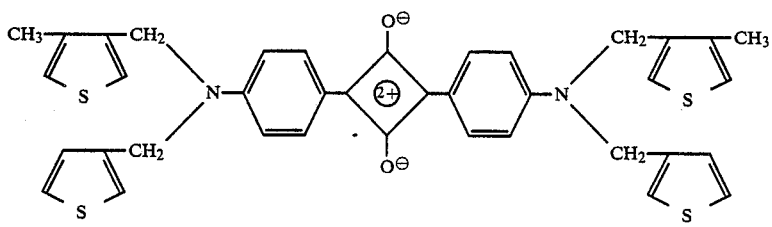

Compound No. I-33

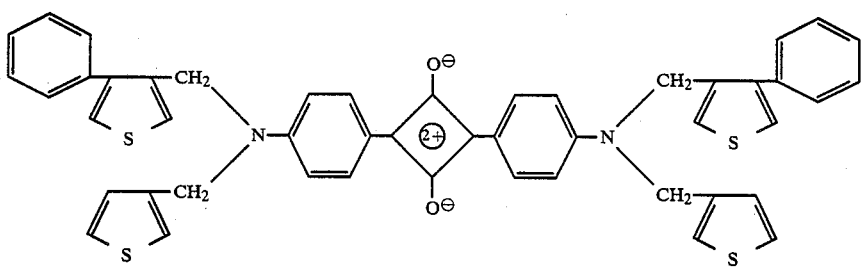

Compound No. I-34

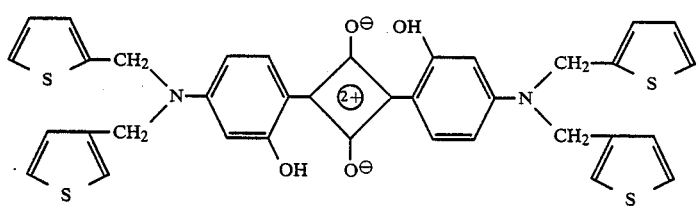

Compound No. I-35

Examples will now be given, wherein various compounds represented by the general formula (I) or (II) were respectively used to produce photoconductors.

EXAMPLE I-1

50 parts by weight of the squarylium compound NO. I-1, 100 parts by weight of a polyester resin (Vylon 200, manufactured by Toyobo Co., Ltd.) and 100 parts by weight of 1-phenyl-3-(p-diethylaminostyryl)-5-(p-diethylaminophenyl)-2-pyrazoline (ASPP) are kneaded with tetrahydrofuan (THF) as a solvent with a mixer for 3 hours to prepare a coating liquid. The coating liquid was applied onto an aluminum-deposited polyester film (Al-PET) as an electroconductive substrate by means of the wire bar technique to form a photosensitive layer having a dry thickness of 15 μm. Thus, a photoconductor was produced.

EXAMPLE I-2

First, a solution of 100 parts by weight of p-diethylaminobenzaldehyde-diphenylhydrazone (ABPH) in 700 parts by weight of tetrahydrofuran (THF) was mixed with a solution of 100 parts by weight of polycarbonate resin (Panlite L-1250) in 700 parts by weight of mixed solvent including the same parts of THF and dichloromethane to prepare a coating liquid. The coating liquid was applied onto an aluminum-deposited polyester film substrate by the wire bar technique to form a charge transporting layer having a dry thickness of 15 μm. 50 parts by weight of the compound No. I-, 50 parts by weight of a polyester resin (Vylon 200), and 50 parts by weight of PMMA were kneaded with a mixer for 3 hours together with THF as a solvent to prepare a coating liquid, which was then applied onto the charge transporting layer by the wire bar technique to form a charge generating layer having a dry thickness of 0.5 μm. Thus, a photoconductor with a structure corresponding to that shown in FIG. 3 was produced.

EXAMPLE I-3

A charge transporting layer was produced by forming a photosensitive layer in substantially the same manneer as in Example I-2 except that α-phenyl-4'-N,N-dimethylaminostilbene, which is a styryl compound, was used to replace ABPH as a charge transporting substance. Then a charge generating layer was formed on the charge transporting layer, thus a photoconductor was produced.

EXAMPLE I-4

A charge transporting layer was produced by forming a photosensitive layer in substantially the same manner as in Example I-2 except that tri(p-toryl)amine, which is a triphenylamine compound, was used to replace ABPH as a charge transporting substance. Then a charge generating layer was formed on the charge

EXAMPLE I-5

A charge transporting layer was produced by forming a photosensitive layer in substantially the same manner as in Example I-2 except that 2,5-bis(p-diethylaminophenyl)-1,3,4-oxadiazole, which is a oxadiazole compound, was used to replace ABPH as a charge transporting substance. Then a charge generating layer was formed on the charge transporting layer, thus a photoconductor was produced.

The electrophotographic characteristics of the five photoconductors thus produced were measured by utilizing an electrostatic recording paper testing apparatus (Kawaguchi Denki Model SP-428).

The surface potential $V_s$ (volts) of each photoconductor is an initial potential which was measured when the surface of the photoconductor was positively charged in the dark by corona discharge at +6.0 kV for 10 seconds. After the discontinuation of the corona discharge, the member was allowed to stand in the dark for 2 seconds, after which the surface potential $V_d$ (volts) of the member was measured. Subsequently, the surface of the photoconductor was irradiated with white light at an illuminance of 2 luxes and the time (seconds) required for the irradiation to decrease the surface potential of the member to half of the $V_d$ was measured, then from which time and the illuminance the half decay exposure amount $E_{\frac{1}{2}}$ (lux·sec) was calculated. Also, the surface potential of the member after 10 seconds of irradiation thereof with white light at an illuminance of 2 luxes was measured as a residual potential $V_r$ (volts).

TABLE 1

| Example | $V_s$ (Volts) | $V_r$ (Volts) | $E_{\frac{1}{2}}$ (lux · sec) |
|---|---|---|---|
| I-1 | 600 | 100 | 6.8 |
| I-2 | 630 | 70 | 6.2 |
| I-3 | 580 | 50 | 5.2 |
| I-4 | 610 | 90 | 6.4 |
| I-5 | 610 | 100 | 7.2 |

As can be seen in Table 1, the photoconductors of Examples I-1, I-2, I-3, I-4 and I-5 have good characteristics in the half decay exposure amounts and the residual potentials.

EXAMPLE I-6

100 parts by weight of each of respective compounds Nos. from I-2 to I-35 and 100 parts by weight of polyester resin (Vylon 200) were kneaded with THF as a solvent with a mixer for 3 hours to prepare a coating liquid. The respective coating liquids were applied on to aluminum substrates to form a photogenerating layer having a dry thickness of about 0.5 μm. Further, the coating liquid prepared in substantially the same manner as in Example I-2, except that the ASPP was used instead of ABPH, was applied on the respective charge generating layer having a thickness of about 15 μm, thus photoconductors were produced.

The electrophotographic characteristics of the photoconductors thus produced were measured by utilizing an electrostatic recording paper testing apparatus SP-428. The results of the measurements are shown in Table 2. The results are obtained as follows. The surface potenccial $V_s$ (volts) of a photoconductor was measured when the surface of a photoconductor was negatively charged at −6.0 kV for 10 seconds. Subsequently, the photoconductor was allowed to stand in the dark for 2 second after the discontinuation of the corona discharge. Thereafter, the surface of the photoconductor was irradiated with white light at an illuminance of 2 luxes and the time (seconds) required to reduce the surface potencial of the photoconductor to a half of the $V_d$ was measured, then from which the half decay exposure amount $E_{\frac{1}{2}}$ (lux·sec) was calculated.

TABLE 2

| Compound No. | $E_{\frac{1}{2}}$ (lux · sec) |
|---|---|
| I-2 | 7.3 |
| I-3 | 6.5 |
| I-4 | 8.9 |
| I-5 | 7.1 |
| I-6 | 6.3 |
| I-7 | 7.9 |
| I-8 | 6.2 |
| I-9 | 6.8 |
| I-10 | 5.2 |
| I-11 | 4.6 |
| I-12 | 6.7 |
| I-13 | 7.9 |
| I-14 | 7.8 |
| I-15 | 8.8 |
| I-16 | 6.3 |
| I-17 | 6.8 |
| I-18 | 6.7 |
| I-19 | 8.2 |
| I-20 | 7.8 |
| I-21 | 7.6 |
| I-22 | 7.8 |
| I-23 | 7.7 |
| I-24 | 8.1 |
| I-25 | 6.8 |
| I-26 | 7.4 |
| I-27 | 6.4 |
| I-28 | 5.5 |
| I-29 | 8.0 |
| I-30 | 9.0 |
| I-31 | 7.4 |
| I-32 | 6.6 |
| I-33 | 6.5 |
| I-34 | 7.9 |
| I-35 | 8.4 |

As can been seen in Table 2, the photoconductors using the respective squarylium compounds Nos. I-2 to I-35 as charge generating substances were also satisfactory with respect to the half decay exposure amount $E_{\frac{1}{2}}$.

The second group of squarylium compounds to be used in the present invention are represented by the following general formula (III).

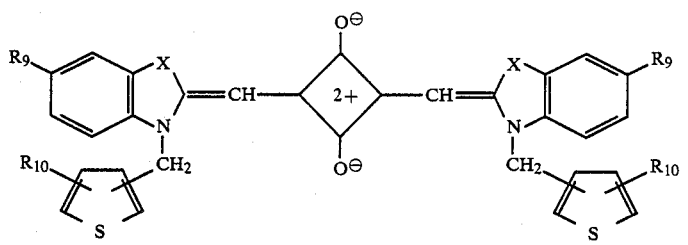
(III)

Wherein, each of $R_9$ and $R_{10}$ stands for a hydrogen atom, a halogen atom, a nitro group, an alkoxy group, an unsubstituted or substituted aryl group, or an unsubstituted or substituted alkyl group; and X stands for an oxygen atom, a sulfur atom, a selenium atom, or a dimethylmethylene group.

These squarylium compounds represented by the general formula (III) can be synthesized according to the following process; that is an amino compound represented by the following formula:

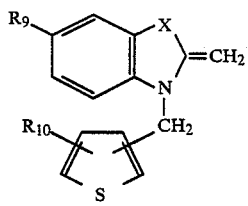

is dyhydration reacted with 3,4-dihydroxy-3-cyclobutene-1,2-dione in a suitable organic solvent such as a mixed solvent of 1-butanol and benzene.

Specific example of squarylium compounds of the general formula (IIIA) of (IIIB) will be shown below, which are partially specified ones of the general formula (III) prepared in the above-mentioned manner.

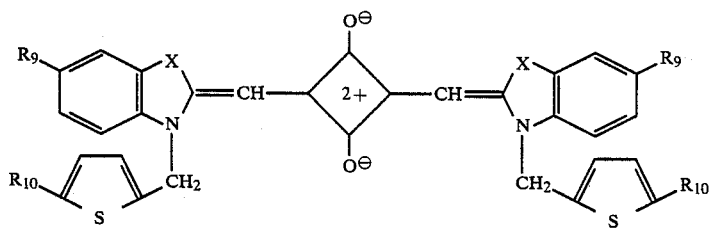
(IIIA)

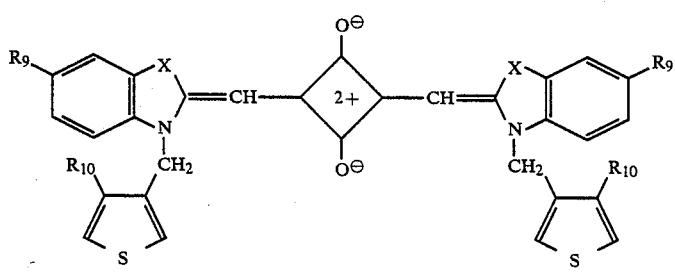
(IIIB)

When $R_9$, $R_{10}$ and X are specified, specific compounds are given. Tables 3 and 4 show specific examples of the compounds represented by the formulae (IIIA) and (IIIB).

TABLE 3

| Compound No. | $R_9$ | $R_{10}$ | X |
|---|---|---|---|
| III-1 | H | H | $CH_3$\\/$CH_3$ −C− |
| III-2 | $CH_3$ | H | $CH_3$\\/$CH_3$ −C− |
| III-3 | $OCH_3$ | H | $CH_3$\\/$CH_3$ −C− |
| III-4 | Cl | H | $CH_3$\\/$CH_3$ −C− |
| III-5 | H | $CH_3$ | $CH_3$\\/$CH_3$ −C− |
| III-6 | H | Ph | $CH_3$\\/$CH_3$ −C− |
| III-7 | $OCH_3$ | $C_2H_5$ | $CH_3$\\/$CH_3$ −C− |
| III-8 | Cl | Br | $CH_3$\\/$CH_3$ −C− |
| III-9 | H | H | O |
| III-10 | H | Cl | O |
| III-11 | H | Ph | O |
| III-12 | H | H | S |
| III-13 | H | H | Se |

TABLE 4

| Compound No. | R$_9$ | R$_{10}$ | X |
| --- | --- | --- | --- |
| III-14 | H | H | $-\underset{\phantom{C}}{C}\underset{CH_3}{\overset{CH_3}{\diagup\!\!\diagdown}}$ |
| III-15 | OCH$_3$ | H | $-\underset{\phantom{C}}{C}\underset{CH_3}{\overset{CH_3}{\diagup\!\!\diagdown}}$ |
| III-16 | Cl | CH$_3$ | $-\underset{\phantom{C}}{C}\underset{CH_3}{\overset{CH_3}{\diagup\!\!\diagdown}}$ |
| III-17 | H | Ph | $-\underset{\phantom{C}}{C}\underset{CH_3}{\overset{CH_3}{\diagup\!\!\diagdown}}$ |
| III-18 | H | H | O |
| III-19 | H | CH$_3$ | O |
| III-20 | H | Ph | O |
| III-21 | H | H | S |
| III-22 | H | CH$_3$ | S |
| III-23 | H | Ph | S |
| III-24 | H | H | Se |
| III-25 | H | CH$_3$ | Se |
| III-26 | H | Ph | Se |

Examples will now be given, wherein various compounds represented by the general formula (III) were respectively used to produce photoconductors.

EXAMPLE II-1

A photoconductor having the structure shown in FIG. 1 and comprising a photosensitive layer having a thickness of 15 μm was produced in substantially the same manner as in Example I-1 except that the compound No. III-1 mentioned above was used instead of the compound No. I-1.

EXAMPLE II-2

Further, a solution of 100 parts by weight of p-diethylaminobenzaldehyde-diphenylhydrazone (ABPH) in 700 parts by weight of tetrahydrofuran (THF) was mixed with a solution of 100 parts by weight of polycarbonate resin (Panlite L-1250) in 700 parts by weight including the same parts of THF and dichloromethane to prepare a coating liquid. The coating liquid was applied onto an aluminum-deposited polyester film substrate by the wire bar technique to form a charge transporting layer having a dry thickness of 15 μm. 50 parts by weight of the compound No. III-1 and 50 parts by weight of a polyester resin (Vylon 200) were kneaded with a mixer for 3 hours together with THF as a solvent to prepare a coating liquid, which was then applied onto the charge transporting layer by the wire bar technique to form a charge generating layer having a dry thickness of 0.5 μm. Thus, a photoconductor with a structure corresponding to that shown in FIG. 3 was produced a convering layer was not provided because it is not directly related to the present invention.

EXAMPLE II-3

A charge transporting layer was produced by forming a photosensitive layer in substantially the same manner as in Example II-2 except that α-phenyl-4'-N,N-dimethylaminostilbene, which is a stilbene compound, was used to replace ABPH as a charge transporting substance. Then a charge generating layer was formed on the charge transporting layer, thus a photoconductor was produced.

EXAMPLE II-4

A charge transporting layer was produced by forming a photosensitive layer in substantially the same manner as in Example II-2 except that tri(p-toryl)amine, which is a triphenylamine compound, was used to replace ABPH as a charge transporting substance. Then a charge generating layer was formed on the charge transporting layer, thus a photoconductor was produced.

EXAMPLE II-5

A charge transporting layer was produced by forming a photosensitive layer in substantially the same manner as in Example II-2 except that 2,5-bis(p-diethylaminophenyl)-1,3,4-oxadiazole, which is an oxadiazole compound, was used to replace ABPH as a charge transporting substance. Then a charge generating layer was formed on the charge transporting layer, thus a photoconductor was produced.

The five photoconductors thus produce were examined with respect to surface potential $V_s$, residual potential $V_r$, and half decay exposure amount $E_{\frac{1}{2}}$ for white light in substantially the same manner as in Example I-1 to I-5. The results of the measurements are shown in Table 5.

TABLE 5

| Example | $V_s$ (Volts) | $V_r$ (Volts) | $E_{\frac{1}{2}}$ (lux · sec) |
| --- | --- | --- | --- |
| II-1 | 610 | 110 | 7.2 |
| II-2 | 630 | 100 | 5.3 |
| II-3 | 630 | 120 | 6.8 |
| II-4 | 650 | 100 | 6.1 |
| II-5 | 620 | 90 | 6.4 |

As can be seen in Table 5, the photoconductors of Examples II-1, II-2, II-3, II-4 and II-5 were satisfactory with respect to surface potential $V_s$, half decay exposure amount $E_{\frac{1}{2}}$, and residual potential $V_r$.

EXAMPLE II-6

100 parts by weight of each of the compounds Nos. III-2 to III-13 shown in Table 3 and the compounds Nos. III-14 to III-26 shown in Table 4 were kneaded with a solution of polyester resin (Vylon 200) and THF as a solvent with a mixer for 3 hours to prepare a coating liquid. The respective coating liquids were applied onto aluminum substrates to form a charge generating layer having a thickness of about 0.5 μm. Further, the coating liquid for a charge transporting layer prepared in substantially the same manner as Example II-2, except that ASPP was used as a charge transporting substance instead of ABPH, was applied on the respective charge generating layer having a thickness of about 15 μm, thus photoconductors were produced.

Photoconductors produced in the above-mentioned manner were examined with respect to electrophotographic characteristics thereof by using the electrostatic recording paper testing apparatus (Kawasaki Denki Model SP-428) in the same manner as in Example I-6 to find respective half decay exposure amounts $E_{\frac{1}{2}}$. The results of the measurements are shown in Table 6.

TABLE 6

| Compound No. | $E_{\frac{1}{2}}$ (lux · sec) |
| --- | --- |
| III-2 | 7.1 |
| III-3 | 6.3 |

TABLE 6-continued

| Compound No. | $E_{\frac{1}{2}}$ (lux · sec) |
| --- | --- |
| III-4 | 8.2 |
| III-5 | 7.0 |
| III-6 | 7.3 |
| III-7 | 6.9 |
| III-8 | 5.2 |
| III-9 | 6.2 |
| III-10 | 6.2 |
| III-11 | 5.6 |
| III-12 | 6.1 |
| III-13 | 7.7 |
| III-14 | 7.2 |
| III-15 | 7.5 |
| III-16 | 6.6 |
| III-17 | 6.1 |
| III-18 | 6.4 |
| III-19 | 8.0 |
| III-20 | 7.5 |
| I-21 | 7.6 |
| I-22 | 7.7 |
| I-23 | 7.0 |
| I-24 | 5.7 |
| I-25 | 6.2 |
| I-26 | 7.3 |

As can be seen in Table 6, the photoconductors using the respective compounds Nos. III-2 to III-26 were satisfactory with respect to the half decay exposure amount $E_{\frac{1}{2}}$.

As described above, according to the present invention, since a squarylium compound represented by any one of the aforementioned chemical formulae is used in a photosensitive layer formed on an electroconductive substrate, as a charge generating substance, a photoconductor shows a high sensitive and excellent characteristics in repreated use when adapted to either a positive charge mode or a negative charge mode. If necessary, a covering layer may be provided on the surface of a photoconductor to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A photoconductor for electrophotography comprising:
   at least one squarylium compound represented by the following general formula (I) as a charge generating substance:

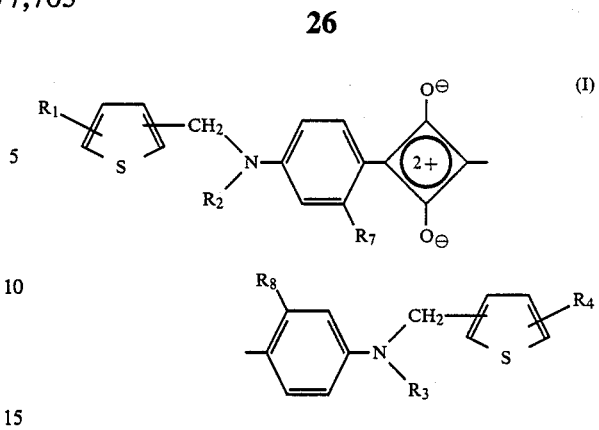

wherein, each of $R_1$, $R_2$, $R_3$ and $R_4$ stands for a hydrogen atom, a halogen atom, an alkyl grup, an aryl group, or a nitro group, and each of $R_7$ and $R_8$ stands for a hydrogen atom or a hydroxy group.

2. A photoconductor as claimed in claim 1, wherein said photoconductor comprises a layer including dispersion of a charge generating substance selected from squarylium compounds represented by the general formula (I) and a charge transporting substance.

3. A photoconductor as claimed in claim 1, wherein said photoconductor comprises a laminate of a charge transporting layer mainly composed of a charge transporting substance and a charge generating layer including a compound selected from squarylium compounds represented by the general formula (I).

4. A photoconductor for electrophotography comprising:
   at least one squarylium compound represented by the following general formula (II) as a charge generating substance:

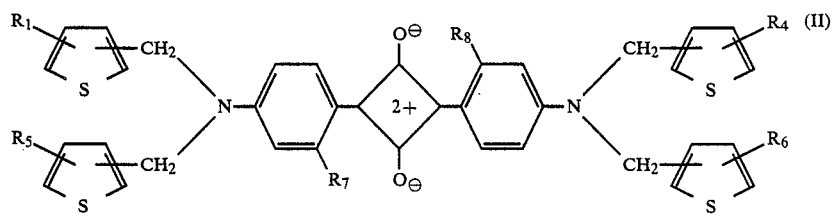

wherein, each of $R_1$, $R_2$, $R_3$, $R_4$, $R_5$ and $R_6$ stands for a hydrogen atom, a halogen atom, an alkyl grup, an aryl group, or a nitro group, and $R_7$ and $R_8$ stands for a hydrogen atom and a hydroxy group, respectively.

5. A photoconductor as claimed in claim 4, wherein said photoconductor comprises a layer including dispersion of a charge generating substance selected from squarylium compounds represented by the general formula (II) and a charge transporting substance.

6. A photoconductor as claimed in claim 4, wherein said photoconductor comprises a laminate of a charge transporting layer mainly composed of a charge transporting substance and a charge generating layer including a compound selected from squarylium compounds represented by the general formula (II).

7. A photoconductor for electrophotography comprising:
   at least one squarylium compound represented by the following general formula (III) as a charge generating substrate:

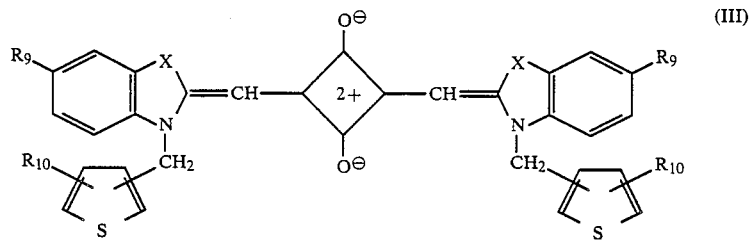

(III)

wherein, each of $R_9$ and $R_{10}$ stands for a hydrogen atom, a halogen atom, a nitro group, an alkoxy group, an unsubstituted or substituted aryl group, or an unsubstituted or substituted alkyl group; X stands for an oxygen atom, a sulfur atom, a selenium atom, or a dimethylmethylene group.

8. A photoconductor as claimed in claim 7, wherein said photoconductor comprises a layer including a dispersion of a charge generating substance selected from squarylium compounds represented by the general formulae (III) and a charge transporting substance.

9. A photoconductor as claimed in claim 7, wherein said photoconductor comprises a laminate of a charge transporting layer mainly composed of a charge transporting substance and a charge generating layer including a compound selected from squarylium compounds represented by the general formulae (III).

* * * * *

UNITED STATES PATENT AND TRADEMARK OFFICE
CERTIFICATE OF CORRECTION

PATENT NO. : 4,877,703
DATED : October 31, 1989
INVENTOR(S) : Masami KURODA ET AL.

It is certified that error appears in the above-identified patent and that said Letters Patent is hereby corrected as shown below: Title page:

Please correct the second priority application of line [30] to read as follows:

-- Apr. 26, 1988 [JP] Japan ....... 63-103678 --

Signed and Sealed this

Eleventh Day of December, 1990

Attest:

HARRY F. MANBECK, JR.

Attesting Officer

Commissioner of Patents and Trademarks